United States Patent
Matsumura et al.

(10) Patent No.: US 7,008,653 B2
(45) Date of Patent: Mar. 7, 2006

(54) METHOD OF DEAMIDATION OF MILK PROTEIN AND METHOD OF DENATURATION OF MILK PROTEIN

(75) Inventors: Yasuki Matsumura, Uji (JP); Tomohiko Mori, Uji (JP)

(73) Assignee: Amano Enzyme Inc., Nagoya (JP)

( * ) Notice: Subject to any disclaimer, the term of this patent is extended or adjusted under 35 U.S.C. 154(b) by 329 days.

(21) Appl. No.: 10/648,806

(22) Filed: Aug. 27, 2003

(65) Prior Publication Data

US 2004/0091575 A1 May 13, 2004

Related U.S. Application Data

(63) Continuation of application No. PCT/JP02/01701, filed on Feb. 26, 2002.

(30) Foreign Application Priority Data

Feb. 27, 2001 (JP) .............................. 2001-052918

(51) Int. Cl.
  A23C 9/12 (2006.01)
  A23C 21/02 (2006.01)
(52) U.S. Cl. ...................................................... 426/42
(58) Field of Classification Search ................. 426/34, 426/42, 656, 580
See application file for complete search history.

(56) References Cited

U.S. PATENT DOCUMENTS

| | | | |
|---|---|---|---|
| 4,687,739 A | 8/1987 | Sugisawa et al. | 435/69 |
| 5,082,672 A | 1/1992 | Hamada et al. | 426/7 |
| 6,756,221 B1 * | 6/2004 | Yamaguchi | 435/227 |

FOREIGN PATENT DOCUMENTS

| | | |
|---|---|---|
| CN | 1240112 A | 1/2000 |
| EP | 0 966 887 A1 | 12/1999 |
| EP | 0 976 829 A2 | 2/2000 |
| JP | 48-75760 | 10/1973 |
| JP | 7-99893 | 4/1995 |
| JP | 2000-050887 | * 2/2000 |

OTHER PUBLICATIONS

Molecular Approaches to Improving Food Quality and Safety, D. Chatnagar and T. E. Cleveland, eds., Van Nostrand Reinhold, New York, 1992, Chapter 2, Shih et al., p. 37-59.
Kato et al., J. Agric. Food Chem., 35, 224-227, 1987.
Motoki et al., Agric. Biol. Chem., 50, 3025-3030, 1986.
J. S. Hamada and W. E. Marshall, J. Food Sci., 54, 598-601 & 635, 1989.
Kikuchi et al., Biochemistry, vol. 10, 1222-1229, 1971.
Gill et al., Ir. J. Food Sci. Technol., vol. 9, 33-41, 1985.
D. Panyam and A. Kilara, Trends in Food Sci. Tech., vol. 7, 120-125, 1996.
Matsumura et al., Food Hydrocol., vol. 8, 555-566, 1994.
Brew et al., Biol. Chem., vol. 245, 4570-4582, 1970.
Kuwajima et al., Biochemistry, vol. 29, 8240-8249, 1990.
Matsumura et al., Journal of the Japanese Society of Food Engineering, vol. 22, No. 2 (2002), P57-64.
Gu et al., J. Agric. Food Chem. 2001, 49, 5999-6005.

* cited by examiner

*Primary Examiner*—Keith Hendricks
(74) *Attorney, Agent, or Firm*—Armstrong, Kratz, Quintos, Hanson & Brooks, LLP (57) ABSTRACT

A method for improving the degree of deamidation (%) and the deamidation rate when deamidating a milk protein by an enzyme which exerts a deamidating effect by acting directly on an amide group of a protein without cleaving a peptide bond or crosslinking the protein is provided. A method for denaturing a milk protein enzymatically is also provided.

A preliminarily denatured milk protein is deamidated by a protein deamidating enzyme which exerts a deamidating effect by acting directly on an amide group of a protein having a molecular weight of 5,000 or more without cleaving a peptide bond or crosslinking the protein. Such an enzyme can be used also for denaturing a milk protein.

14 Claims, 4 Drawing Sheets

METHOD OF DEAMIDATION OF MILK PROTEIN AND METHOD OF DENATURATION OF MILK PROTEIN

CROSS REFERENCE TO RELATED APPLICATIONS

This application is a continuation of international application No. PCT/JP02/01701, filed Feb. 26, 2002, which claims priority to Japanese application No.2001-052918, filed Feb. 27, 2001.

FIELD OF THE INVENTION

The present invention relates to a method for deamidating a milk protein utilizing an enzyme which exerts a deamidating effect by acting directly on an amide group of a protein without cleaving a peptide bond or crosslinking the protein as well as a method for producing a deamidated milk protein. The present invention also relates to a method for denaturing a milk protein and a method for producing a protein degradation product, both utilizing said enzyme.

BACKGROUND OF THE INVENTION

Generally, the negative charge of a protein is increased when glutamine and asparagine residues in the protein are deamidated to generate carboxyl groups, resulting in a reduced isoelectric point and an increased hydrating ability. In addition, an increased static repelling force leads to a reduced interaction between proteins, i.e., a reduced associating property. Such changes allow the solubility and the water dispersibility of the protein to be increased greatly. Furthermore, the increased negative charge on the protein serves to unfold the protein conformation, changes the higher structure, and allows a hydrophobic region which was buried initially deep inside the molecule to be exposed on the surface of the molecule. Accordingly, the deamidated protein is imparted with an amphiphilic property, and serves as an ideal surfactant which gives a great improvement in the protein's emulsifying ability, emulsion stability, foaming performance and foam stability.

Thus, the deamidation of a protein leads to the improvement in various functions and characteristics of the protein, and the utility of the protein is far greatly enhanced (for example, see Molecular Approaches to Improving Food Quality and Safety, D. Chatnagar and T. E. Cleveland, eds., Van Nostrand Reinhold, New York, 1992, p.37).

Three methods for deamidating proteins enzymatically are known, including a protease treatment under a high pH (pH 10) condition (A. Kato, A. Tanaka, N. Matsudomi and K. Kobarashi, J. Agric. Food Chem., 35, 224, 1987), a transglutaminase method (M. Motoki, K. Seguro, A. Nio and K. Takinami, Agric. Biol. Chem., 50, 3025, 1986), and a peptide glutaminase method (UP 5082672A and J. S. Hamada and W. E. Marshall, J. Food Sci., 54, 598, 1989), which involve the following problems.

In the protease method, it is impossible to avoid a peptide bond cleavage, which is a primary reaction of the method, and by which the improvement in the function of the protein expected as a result of a deamidation is limited (especially the foam stability is reduced). It is also disadvantageous that a bitter taste occurs.

In the transglutaminase method, a crosslinking reaction as a result of an isopeptide bond formation between glutamine and lysine, which is a primary reaction of the method, should be suppressed by means of a preliminary chemical protection of an $\epsilon$-amino group of the lysine residue. Accordingly, the production of an edible deamidated protein by this method requires a procedure in which a reversible protective group such as a citraconyl group is used previously as a protective group prior to the deamidation of glutamine and a subsequent deprotection should be followed further by the separation of a deamidated protein from liberated citraconic acid. Thus, this method is far less practical due to its complicated manufacturing process and poor cost efficiency as described above.

On the other hand, the peptide glutaminase method requires a protein hydrolysate (U.S. Pat. No. 5,082,672A and J. S. Hamada and W. E. Marshall, J. Food Sci., 54, 598, 1989) since the enzyme catalyzes mainly the deamidation of a peptide whose molecular weight is reduced and can not act as itself on a protein (M. Kikuchi, H. Hayashida, E. Nakano and K. Sakaguchi, Biochemistry, Vol. 10, 1222–1229, 1971 and B. P. Gill, A. J. O'Shaughnessey, P. Henderson and D. R. Headon, Ir. J. Food Sci. Technol., Vol. 9, 33–41, 1985). Thus, the concomitant use of a protease can not be avoided, and a bitter taste occurs as is experienced in the protease method described above, together with problematic peptide formation and reduction in functions, especially in the foam stability.

As a method for overcoming such problems, a method for deamidating a protein (JP-A-2000-50887) is disclosed which employs an enzyme which exerts its deamidation effect by acting directly on a protein (protein deamidating enzyme).

On the other hand, a method involving a protein denaturation by a treatment for example with heat or a denaturing agent is also known. The significance of the denaturation of a protein may for example be an improvement in the sensitivity of a protease, improvement in the digestibility, as well as an improvement in the protein functions such as the emulsification characteristics, foam characteristics and gelling characteristics. In the prior art, it is ordinary to denature a protein by a physical method or a chemical method. A physical method may for example be a heat treatment or a high pressure treatment. A chemical method may for example be a treatment with a denaturing agent (urea, guanidine hydrochloride), reducing agent, oxidant, acid and alkali.

SUMMARY OF THE INVENTION

As described above, 4 techniques were proposed as methods for deamidating proteins. Among them, the deamidation method employing an enzyme which exerts its deamidating effect by acting directly on a protein (protein deamidating enzyme) is superior to other three methods since it enables the deamidation using a protein as it is without any previous degradation or chemical modification of the protein.

Nevertheless, this enzyme was examined for its effect, and the results indicated that it can act on almost all proteins to effect a deamidation but its deamidation rate or degree of deamidation (%) varied depending on the types of the proteins, some of which could not sufficiently be deamidated. Thus, it involves problems to be overcome with regard to the deamidation rate or the degree of deamidation (%).

The first aspect of the invention is established in view of the problems described above, and is intended to improve the deamidation rate or the degree of deamidation (%) in a deamidating method employing a protein exerting a deamidating effect by acting directly on an amide group of a protein without cleaving a peptide bond or crosslinking the protein.

On the other hand, as described above a prior art protein denaturation usually employs a physical method or chemical method. However, such a physical method or chemical method involves a protein degradation, side chain destruction, aggregation and insolubilization, which may be disadvantageous in an industrial application such as a food industry. Accordingly, a method for denaturing a protein using an enzyme has been sought. A method employing an enzyme exhibits a higher reaction selectivity when compared with a physical or chemical method and can be conducted under a gentle condition, which reduces undesirable side reactions and also reduces the energy consumption, whereby being regarded as a superior method to the physical or chemical method. Especially, an enzymatic method capable of being conducted under a gentle condition is advantageous since it is not accompanied by undesirable side reaction or excessive denaturation and also since it may provide a denaturation condition which is favorable for exerting the functions such as emulsification and foaming properties, whereby being regarded to have a high industrial applicability. Nevertheless, there is no currently known suitable enzymatic denaturation method.

The second aspect of the invention is established based on the problems described above, and intended to provide a method for denaturing a protein using an enzyme.

We made various investigation in view of the problems in relation to the first aspect of the invention. First, α-lactoglobulin as a protein which had not been deamidated sufficiently when being subjected directly to the protein deamidating enzyme described above was investigated in an attempt to improve the deamidation rate and the degree of deamidation (%). As a result, it was found that by using an α-lactoglobulin which had previously been denatured prior to the deamidation the deamidation rate and final degree of deamidation (%) were improved markedly. Such findings serve as a basis of the first aspect of the invention, which is composed of as described below. Thus, the invention is:

a method for deamidating a protein (such as a milk protein) comprising bringing a denatured protein (such as a denatured milk protein) into contact with an enzyme which exerts a deamidating effect by acting directly on an amide group of a protein without cleaving a peptide bond or crosslinking the protein.

We also investigated the characteristics of a protein which had been deamidated by a protein deamidating enzyme. We also conducted a spectroscopic analysis, and the results indicated that the tertiary structure of the deamidated protein had substantially been destroyed, i.e., the protein had been denatured. In addition, it was also found that the secondary structure of such a deamidated protein was preserved in spite of the destruction of the tertiary structure. Such a denatured state is known to be a structure preferable for exerting the functions such as the emulsification property and the foaming property (D. Panyam and A. Kilala, Trends in Food Sci. Tech., Vol. 7, 120–125, 1996). In addition, a deamidated protein was also found to have been improved greatly in terms of the sensitivity to a protease. Such findings serve the basis of the second aspect of the invention, which is composed of as described below. Thus, the invention is:

a method for denaturing a protein (such as a milk protein) comprising bringing a protein (such as a milk protein) into contact with an enzyme which exerts a deamidating effect by acting directly on an amide group of a protein without cleaving a peptide bond or crosslinking the protein.

BRIEF DESCRIPTION OF THE DRAWINGS

These and other objects and technical advantages of the present invention will be readily apparent from the following description of the preferred exemplary embodiments of the invention in conjunction with the accompanying drawings, in which.

"●" indicates the non-denatured α-lactoalbumin, while "○" indicates the denatured α-lactoalbumin.

"A" is a graph in the presence of 2 mM ethylene diamine tetraacetic acid, "B" is a graph in the presence of 2 mM $CaCl_2$, "Native" represents a non-denatured α-lactoalbumin, "D20" represents a deamidated α-lactoalbumin of 20% deamidation degree, "D55" represents a deamidated α-lactoalbumin of 55% deamidation degree and "D61" represents a deamidated α-lactoalbumin of 61% deamidation degree.

"A" is a graph in the presence of 2 mM ethylene diamine tetraacetic acid, "B" is a graph in the presence of 2 mM $CaCl_2$, "Native" represents a non-denatured α-lactoalbumin, "D20" represents a deamidated α-lactoalbumin of 20% deamidation degree, "D55" represents a deamidated α-lactoalbumin of 55% deamidation degree and "D61" represents a deamidated α-lactoalbumin of 61% deamidation degree.

"A" represents a non-treated α-lactoalbumin, "B" represents a deamidated α-lactoalbumin. Lanes 1, 2, 3, 4 and 5 represent the samples treated with trypsin for periods of 0.5, 1, 2, 4, and 24 hours, respectively.

DETAILED DESCRIPTION OF THE INVENTION

The first aspect of the invention is a method for deamidating a protein (such as a milk protein) comprising bringing a denatured protein (such as a denatured milk protein) into contact with an enzyme which exerts a deamidating effect by acting directly on an amide group of a protein without cleaving a peptide bond or crosslinking the protein.

A denatured protein according to the invention can be prepared by denaturing a non-denatured protein by a known denaturation method. A denaturation method may for example be a physical denaturation method such as a treatment with heat or pressure, a chemical denaturation method such as a treatment with an acid, alkali, denaturing agent (urea, guanidine hydrochloride, surfactant and the like), oxidant, reducing agent, chelating agent and the like. Any of these treatments may be conducted alone or any two or more can be conducted simultaneously or at a certain time interval. For example, a denaturing agent is added to a protein solution and then the solution is heated. As a result, the denaturation with the denaturing agent and the denaturation with heat can be effected simultaneously.

The denaturing treatment can be selected in view of the type of the protein to be denatured or necessary denaturation degree.

The preparation of a denatured protein can be conducted simultaneously with the reaction with a protein deamidating enzyme described below. For example, a denaturing agent is added to a solution containing a protein and a protein deamidating enzyme described below and the reaction with the protein deamidating enzyme described below is conducted in the presence of a denaturing agent.

A protein according to the invention is not only a simple protein consisting only of amino acid residues but also a conjugated protein and the like which is a complex with a saccharide, lipid and the like. The molecular weight is preferably 5,000 or more, especially 10,000 to 2,000,000.

For example, a vegetable protein may be a protein derived from a bean or cereal, an animal protein may be a milk protein such as casein and β-lactoglobulin, egg protein such as ovalbumin, meat protein such as myosin and actin, blood protein such as serum albumin, tendon protein such as gelatin and collagen. Proteins partially decomposed by a chemical treatment with an acid or alkali or an enzymatic treatment and proteins modified chemically by various reagents may also be employed.

An enzyme employed in a method according to the invention (hereinafter referred to as a protein deamidating enzyme) exerts a deamidating effect by acting directly on an amide group of a protein without cleaving a peptide bond or crosslinking the protein (hereinafter referred to as a protein deamidating effect). As far as such an effect is possessed, the type of the enzyme is not limited particularly.

A protein deamidating enzyme according to the invention is preferably one having a deamidating effect on a protein (denatured protein) having a molecular weight of 5,000 or more, especially one having a deamidating effect on a protein (denatured protein) having a molecular weight of 10,000 to 2,000,000.

A protein deamidating enzyme can be one prepared from a culture medium of a microorganism producing a protein deamidating enzyme. Such a microorganism employed for preparing the protein deamidating enzyme is not limited particularly but may be a microorganism which produces the relevant enzyme in the culture medium, including microorganisms belonging to a genus of *Chryseobacterium, Flavobacterium, Empedobacter, Sphingobacterium, Aureobacterium* or *Myroides*. It is preferred especially to use, in the preparation of a protein deamidating enzyme, a microorganism *Chryseobacterium* sp. No.9670 belonging to the genus of *Chryseobacterium. Chryseobacterium* sp. No. 9670 has been deposited under the accession number FERM BP-7351 (transferred from the domestic deposition under the accession number FERM P-17664 based on the request of the transfer dated Nov. 8, 2000) in National Institute of Bioscience and Human-Technology of Agency of Industrial Science and Technology of Ministry of International Trade and Industry (current National Institute of Bioscience and Human-Technology of National Institute of Advanced Industrial Science and Technology of Ministry of Economy, Trade and Industry).

A method for preparing a protein deamidating enzyme from the culture medium of a microorganism described above may be a known protein separation and purification method (centrifugation, UF concentration, salting-out, ion exchange resin chromatography and the like). For example, a culture medium is centrifuged to remove cells, and then subjected to a salting-out together with chromatography and the like as appropriate, whereby obtaining an intended enzyme.

In the invention, a denatured protein described above is brought into contact with a protein deamidating enzyme described above. The denatured protein may be subjected to the reaction in the form of a solution, slurry or paste. A fluid containing the denatured protein may not only be an aqueous solution but also an emulsion with a fat. Furthermore, it is also possible to add various additives to the solution, including other proteins, salts, saccharides, flavors, water retainers, colorants and the like. A solution containing a denatured protein may be prepared by denaturing a protein in a solution containing said protein in a non-denatured form, or by producing a denatured protein in advance and then dissolving in a suitable solvent.

The reaction condition of a protein deamidating enzyme (amount of the enzyme, reaction time, temperature, reaction pH and the like) is not limited particularly, an ordinary condition employs the enzyme in an amount of 0.1 to 100 units, preferably 1 to 10 unites per g of the protein, in the reaction at a temperature usually of 5 to 80° C., preferably 20 to 60° C., at a pH usually of 2 to 10, preferably 4 to 8, for a period 10 seconds to 48 hours, preferably 10 minutes to 24 hours. Such a condition may vary depending on the purity of the enzyme employed, type and purity of the denatured protein and the like.

As described above, by bringing a denatured protein into contact with a protein deamidating enzyme the amide group in the denatured protein can be directly deamidated. As a result, the deamidated protein thus formed has been highly deamidated, and imparted with an increased negative charge which leads to a reduced pI, increased hydrating performance and increased static repelling force. In addition, the change in the higher structure of the protein gives an increased surface hydrophobicity. As a result of these effects, an improvement is accomplished in the protein functions, such as the solubility and dispersibility, foaming performance and foam stability, emulsifiability and emulsion stability.

A protein whose functions have been improved as described above now has a wide applicability mainly to a food industry. Since most of vegetable proteins have poor functions in terms of the solubility, dispersibility and emulsifiability at a weakly acidic pH associated with an ordinary food product, their use is limited when incorporated into most of the food products such as an acidic beverage including coffee whiteners and juices as well as dressings, mayonnaises, creams and the like. Nevertheless, by deamidating a hardly-soluble vegetable protein such as a wheat gluten by an inventive method, the solubility and the dispersibility are enhanced, whereby enabling the use in a food product which has not previously been suitable for incorporation, as in the case of a highly dispersible batter for deep-fried foods.

It is also possible to use the inventive method for the purpose of improving the dough texture in the field of bakery and confectionery. For example, a dough having a high gluten content has a poor extending ability, poses problems in its handling or mechanical characteristics, and gives a final bread product whose mass and quality are still problematic. By deamidating the gluten in a manner of the present invention, the extending ability is improved and the problems described above can be overcome. The deamidated gluten also serves as an emulsifier, whereby improving the bakery characteristics such as the shelf life and softness. Furthermore, a dough containing a deamidated gluten is suitable for producing crackers, biscuits, cookies, pizza and pie crust since it has a low plasticity and an excellent extending ability, and the inventive method can be also applicable to the production of such food products.

It is also possible to use an inventive method to treat a protein which causes an allergy or intolerance to a protein contained in a food or causes a genetic diseases, whereby removing or reducing the toxicity or allergenicity.

Moreover, an inventive method can be used to reduce the mineral sensitivity of a protein, whereby increasing the soluble mineral level in a protein/mineral solution and increasing the absorption of the mineral into a human body. Generally, the absorption of a calcium in a food is known to be promoted by solubilizing the calcium using an organic acid or casein phosphopeptide. In a similar mechanism, a large amount of calcium can be solubilized by deamidating a protein by an inventive method. It is also possible to use such a deamidated protein to produce a high mineral (for example, calcium) beverage or mineral (for example, calcium) absorption promoter.

Also in the production of an amino acid-based seasoner (hydrolyzed animal protein (HAP), hydrolyzed vegetable protein (HVP)) or miso/soy sauce, advantageous effects are accomplished such as the reduction in bitterness, the increase in the % degradation by a protease, the enhancement of the glutamic acid content and the like. It is well known that a bitter taste is resulting from a hydrophobic peptide, and such a bitter peptide can be reduced by the deamidation. It is also known that a peptide having a glutamic acid on its N-terminal has a bitterness-masking effect.

In addition, the present-invention can be utilized in modifying the functions of a protein. When the protein to be deamidated is an enzyme, then the enzymo-chemical or physicochemical characteristics can be modified. For example, an enzyme protein is deamidated by an inventive method to reduce the isoelectric point of the enzyme protein, whereby modifying the pH stability. It is also possible that by changing the structure or the electric environment of an active site, the substrate affinity, substrate specificity, reaction rate, pH dependency, temperature dependency, temperature stability of the relevant enzyme can also be modified.

Furthermore, a use can be made for improving the efficiency of the extraction or concentration of a cereal or bean protein. Generally, a protein derived from a cereal or bean such as wheat or soybean is mostly insoluble, and is difficult to extract the protein therefrom, but it becomes possible, when a suspension of a wheat powder or soybean powder is solubilized by an inventive method, to extract the protein easily and also a high content protein isolate can be obtained.

In the case of a soybean protein, the protein is extracted from a defatted soybean powder or flake (protein content of about 50%) usually by insolubilizing the protein by means of a heat treatment, ethanol treatment or isoelectric point treatment at about pH 4.5 followed by removing any soluble saccharides to obtain a soybean protein concentrate whose protein content is about 70%. When a protein having a further higher purity is desired, then the soybean powder or concentrate is suspended or dissolved in a dilute alkali to effect the dissolution of the protein, from which any insoluble matters are removed. The resultant preparation is named as a soybean protein isolate, which contains the protein at about 90%. Such soybean protein products are employed in various food product by virtue of their functions such as the soybean protein emulsifiability, gelling performance and water retaining ability as well as high nutrition values, including hams, sausages, baby foods and the like.

By applying the present invention to the production of such a soybean protein product, the improvement in the protein dissolution gives not only an increased yield but also a protein product at a high concentration. A protein product thus obtained exhibits excellent functions since it has been deamidated. Accordingly, it exhibits excellent effects when incorporated into various food products such as processed meet and fish products and noodles, and enables the production of a food having novel textures and functions.

The first aspect of the invention includes a method for producing a deamidated protein comprising a step for denaturing a protein (such as a milk protein) and a step for deamidating a denatured protein (such as a denatured milk protein) obtained in the previous step by bringing said denatured protein (such as a denatured milk protein) into contact with an enzyme which exerts a deamidating effect by acting directly on an amide group of a protein without cleaving a peptide bond or crosslinking the protein.

The second aspect of the invention is discussed below. As described above, the second aspect of the invention is a method for denaturing a protein (such as a milk protein) comprising bringing a protein (such as a milk protein) into contact with an enzyme which exerts a deamidating effect by acting directly on an amide group of a protein without cleaving a peptide bond or crosslinking the protein.

In this context, an enzyme which exerts a deamidating effect by acting directly on an amide group of a protein without cleaving a peptide bond or crosslinking the protein means a protein deamidating enzyme described above, which is preferably one having a deamidating effect on a protein (denatured protein) having a molecular weight of 5,000 or more, especially one having a deamidating effect on a protein (denatured protein) having a molecular weight of 10,000 to 2,000,000, similarly to the first aspect of the invention. The effect of the protein deamidating enzyme and the method for producing is as described above.

In the second aspect of the invention, such a protein deamidating enzyme is allowed to act on a protein to deamidate the protein, whereby effecting the denaturation. The protein in this context is not only a simple protein consisting only of amino acid residues, but also a conjugated protein which is a complex with a saccharide, lipid and the like, as is in the case of the first aspect of the invention. The molecular weight is preferably 5,000 or more, especially 10,000 to 2,000,000. For example, a vegetable protein may be a protein derived from a bean or cereal, an animal protein may be a milk protein such as casein and β-lactoglobulin, egg protein such as ovalbumin, meat protein such as myosin and actin, blood protein such as serum albumin, tendon protein such as gelatin and collagen. Proteins partially decomposed by a chemical treatment with an acid or alkali or an enzymatic treatment and proteins modified chemically by various reagents may also be employed.

The protein may be subjected to the reaction in the form of a solution, slurry or paste. A fluid containing the protein may not only be an aqueous solution but also an emulsion with a fat. Furthermore, it is also possible to add various additives to the solution, including other proteins, salts, saccharides, flavors, water retainers, colorants and the like.

The reaction condition of a protein deamidating enzyme (enzyme level, reaction time, temperature, reaction pH) is not limited particularly, an ordinary condition employs the enzyme in an amount of 0.1 to 100 units, preferably 1 to 10 unites per g of the protein, in the reaction at a temperature usually of 5 to 80° C., preferably 20 to 60° C., at a pH usually of 2 to 10, preferably 4 to 8, for a period 10 seconds to 48 hours, preferably 10 minutes to 24 hours. Such a condition may vary depending on the purity of the enzyme employed, type and purity of the protein and the like.

As described above, by bringing a protein into contact with a protein deamidating enzyme, the protein can be denatured. Thus, a denatured protein is obtained. This denatured protein has a high sensitivity to a protease. Accordingly, this denatured protein gives a protein degradation product efficiently when being subjected to the action of a protease. Such a method for producing a protein degradation product is also encompassed by the invention, and one encompassed typically is a method for producing a protein degradation product comprising a step for denaturing a protein by a method described above and a step for bringing a denatured protein obtained in the previous step into contact with a protease.

Such a protease may for example be any known protease such as pepsin, trypsin, papain and the like. A protease employed may be selected appropriately on the basis of the type of the protein to be degraded and the physical state of the protein degradation product. The reaction condition of a protease (amount of the enzyme, reaction time, temperature, reaction pH and the like) may be also selected appropriately on the basis of the type, state and amount of the protein to be degraded.

A method according to the second aspect of the invention can be applied to various food product similarly to the invention of the first aspect for the purpose of improving the function of proteins in a food product, such as the solubility, dispersibility, foaming performance, foam stability, emulsifiability, emulsion stability and the like. It is also utilizable for eliminating or reducing any allergenicity of a protein in a bakery or confectionery product. Moreover, it can be utilized for modifying the taste of an amino acid-based seasoning and the like.

On the other hand, by applying the second aspect of the invention, it becomes possible to solve one of the problems associated with the production of an enzymatic HAP (hydrolyzed animal protein) and hydrolyzed vegetable protein (HVP) which is experienced as a low % degradation, since it becomes possible to increase the sensitivity of a protein to a protease.

The first and second aspects of the invention are described below in the following Examples which are not intended to restrict the invention.

EXAMPLE 1

Preparation of Protein Deamidating Enzyme

*Chryseobacterium* sp. No. 9670 (FERM-7351 as an accession number by National Institute of Bioscience and Human-Technology of Agency of Industrial Science and Technology of Ministry of International Trade and Industry) was cultured in an LB Base medium at 25° C. to obtain a 40-hour culture medium, which was made free from cells by centrifugation at 4° C. and 12000 rpm (222000×g) for 20 minutes to obtain a supernatant, which was passed through an ultrafiltration membrane to effect a 25-fold concentrating, followed by lyophilization to obtain a crude enzyme powder. This was dissolved in a 10 mM sodium phosphate buffer (pH 6.5) containing 2.0 M NaCl, made free of insolubles by centrifugation at 4° C. and 10000 rpm (12300×g) for 15 minutes to obtain a supernatant, which was subjected to a phenyl sepharose CL-6B column (Pharmacia) equilibrated with a 10 mM sodium phosphate buffer (pH 6.5) containing 2.0 M NaCl to elute the adsorbed protein with a linear gradient of NaCl from 2.0 M to 0 M.

The protein deamidation activity fractions were collected, concentrated using an ultrafiltration membrane, subjected to a sephacryl S-100 column equilibrated with a 10 mM sodium phosphate buffer (pH 6.5) containing 0.6M NaCl and 0.05% Tween 20 and then eluted with the same buffer. The following method is employed to measure the enzymatic activity of each fraction, and the protein deamidation activity fractions were collected and concentrated using an ultrafiltration membrane to obtain a protein deamidation enzyme solution.

When the following methods (employing Z-Gln-Gly and casein as substrates) were employed to measure the activity, the enzyme preparations were obtained to have the activities of 33.7 units/ml (Z-Gln-Gly as a substrate) and 13.5 units/ml (casein as a substrate).

Enzyme activity assay: The enzyme activity assay was conducted as described below using Z-Gln-Gly and casein as substrates.

Activity measurement: 10 µl of an enzyme solution was added to 100 µl of a 176 mM phosphate buffer (pH 6.5) containing 10 mM Z-Gln-Gly, incubated for 60 minutes at 37° C., combined with 100 µl of a 12% trichloroacetic acid solution to quench the reaction. After centrifugation (15000 rpm, 4° C., 5 minutes), the supernatant was measured using an F-kit ammonia (Boehringer Mannheim) as described below (A1). Separately, water was employed measured instead of the enzyme solution and measurement was performed in the similar manner (A2).

100 µl of F-kit ammonia Reagent 2 was combined with 10 µl of the supernatant and 190 µl of water and allowed to stand at room temperature for 5 minutes, and a 100 µl aliquot was subjected to the measurement of the absorbance at 340 nm (E1). The remaining 200 µl was combined with 1.0 µl of Reagent 3 (glutamate dehydrogenase), allowed to stand for 20 minutes at room temperature, and then 200 µl of the remainder was subjected to the measurement of the absorbance at 340 nm (E2).

The quantity of the enzyme which liberates 1 µmol of ammonia per minutes under the condition specified above was regarded as 1 unite, and the following equation was applied.

$$U/ml = 1.76 \times [A1(E1-E2) - A2(E1-E2)]$$

As a substrate, a 1% casein (Hammarsten, Merck) was employed instead of the 10 mM Z-Gln-Gly to measure the activity, whereby verifying the action on an amide group binding to the protein.

EXAMPLE 2

Figure 1:
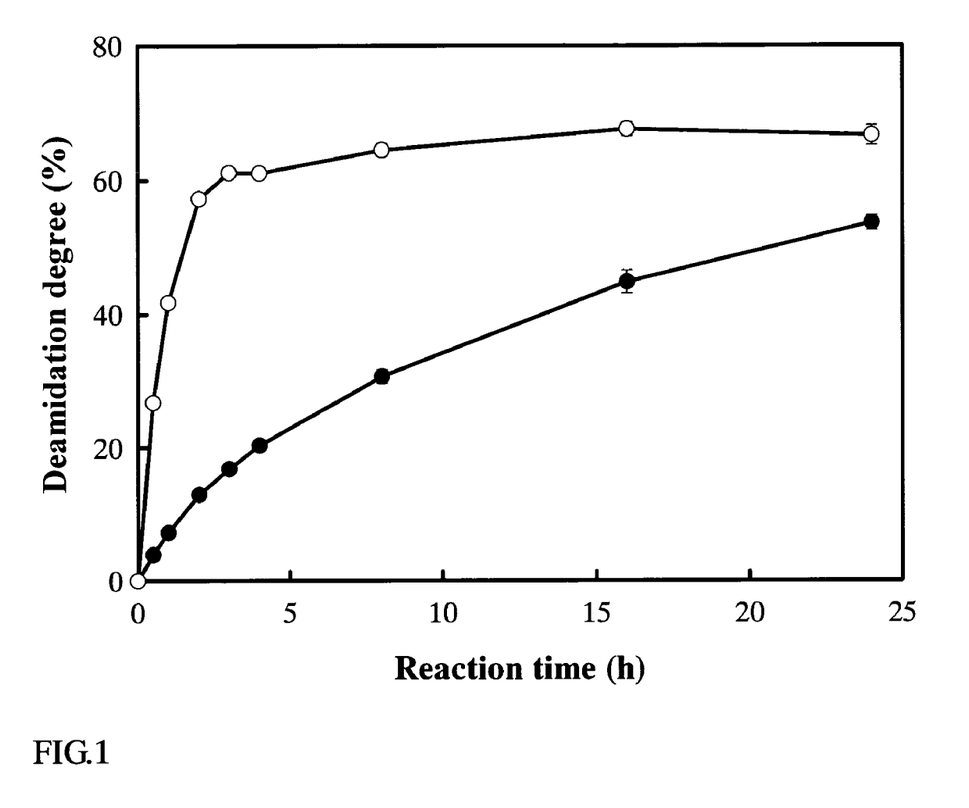
FIG. 1 shows the time course of the deamidating reaction by a protein deamidating enzyme with a denatured or non-denatured α-lactoalbumin in Example 2.

Treatment of Denatured α-lactoalbumin with Protein Deamidating Enzyme

α-Lactoalbumin (Sigma) was dissolved at 10 mg/ml in a 20 mM Tris-HCl buffer (pH 7.0), to which the protein deamidating enzyme obtained in Example 1 was added at 1.82 µg/ml and shaken at 42° C. For the purpose of denaturing the α-lactoalbumin, a 5 mM ethylenediamine tetraacetic acid was added as a denaturing agent (chelating agent) (Matsumara et al., Food Hydrocol., Vol.8, 555–566, 1994) whereby effecting a deamidation reaction. The time course of the reaction was as shown in FIG. 1. In this figure, the degree of deamidation (%) represents the ratio of the glutamine residue which has been deamidated based on the total glutamine residue in the protein. The total glutamine residue number was obtained on the basis of the total amino acid sequence of the α-lactoalbumin (Brew et al., J. Biol. Chem., Vol. 245, 4570–4582, 1970), and the deamidated glutamine residue number was obtained from the quantity of ammonia liberated during the reaction.

As described above, the denaturation of the α-lactoalbumin (conversion into a molten globule state) was revealed to remarkably promote the deamidation by the protein deamidating enzyme. Thus, the degree of deamidation of the native α-lactoalbumin was 20% at 4 hours and 55% at 24 hours, while that of the denatured α-lactoalbumin (in a molten globule state) was 61% at 4 hours and 66% at 24 hours. The results indicated that the deamidation rate and the final degree of deamidation were both improved.

EXAMPLE 3

Figure 2:
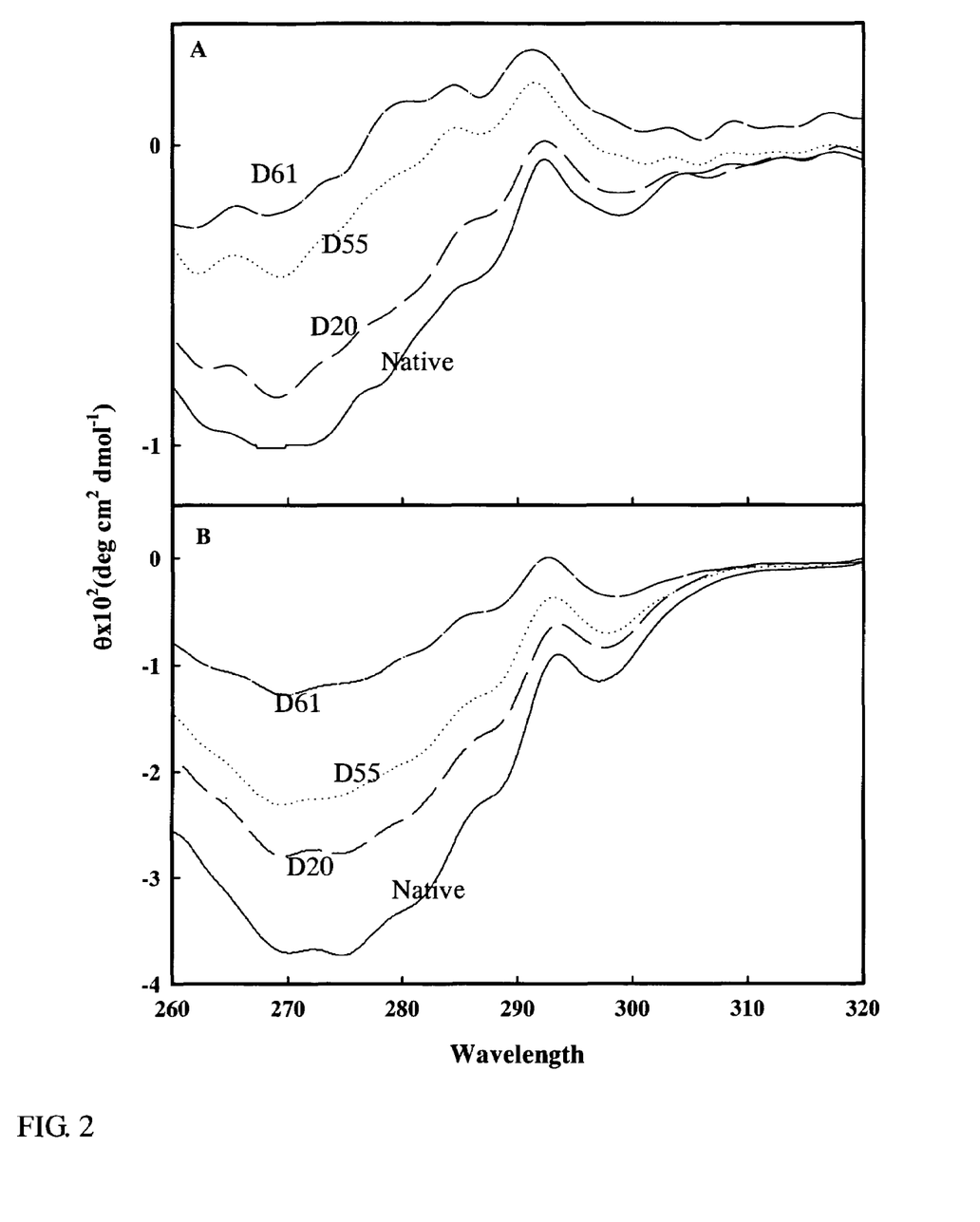
FIG. 2 shows a near UV circular dichroism analytical spectrum of the deamidated α-lactoalbumin in Example 3.

Change in Higher Structure of α-lactoalbumin Treated with Protein Deamidating Enzyme The change in the higher structures of the deaminized α-lactoalbumins obtained in Example 2 which had various degrees of deamidation (D20: 20% deamidation degree, D55: 55% deamidation degree, D61: 61% deamidation degree) were examined by a near UV CD (circular dichroism), and the results obtained are shown in FIG. 2. The analysis was conducted in a 20 mM Tris-HCl buffer (pH 7.0) containing 2 mM ethylenediamine tetraacetic acid (FIG. 2A) or 2 mM $CaCl_2$ (FIG. 2B). As a control, a non-deamidated α-lactoalbumin (Native) was employed. As a result, the spectrum intensity of the deamidated α-lactoalbumin at around 270 nm was reduced in any of the solution. The degree of this reduction was increased when the degree of deamidation was increased. These findings suggest that the deamidation allowed the aromatic group on the side chain of the α-lactoalbumin to be remote, i.e., served to deteriorate the tertiary structure. The degree of this deterioration of the tertiary structure was increased when the degree of deamidation was increased. It is generally known that the α-lactoalbumin undergoes the deterioration of the tertiary structure in the presence of ethylenediamine tetraacetic acid while it is stabilized in the presence of calcium (Kuajima et al., Biochemistry, Vol. 29, 8240–8249). This is reflected also by the fact that the spectrum of the non-deamidated α-lactoalbumin (native) exhibited a great reduction in the intensity in the presence of ethylenediamine tetraacetic acid when compared with that in the presence of $CaCl_2$. Since the spectrum intensity of the highly deamidated α-lactoalbumin in the presence of calcium (D61 in FIG. 2B) was almost similar to the spectrum intensity of the non-deamidated α-lactoalbumin in the presence of ethylenediamine tetraacetic acid (Native in FIG. 2A), it was suggested that the change in the tertiary structure by the deamidation was so substantial that it was no longer stabilized even by the presence of calcium.

Figure 3:
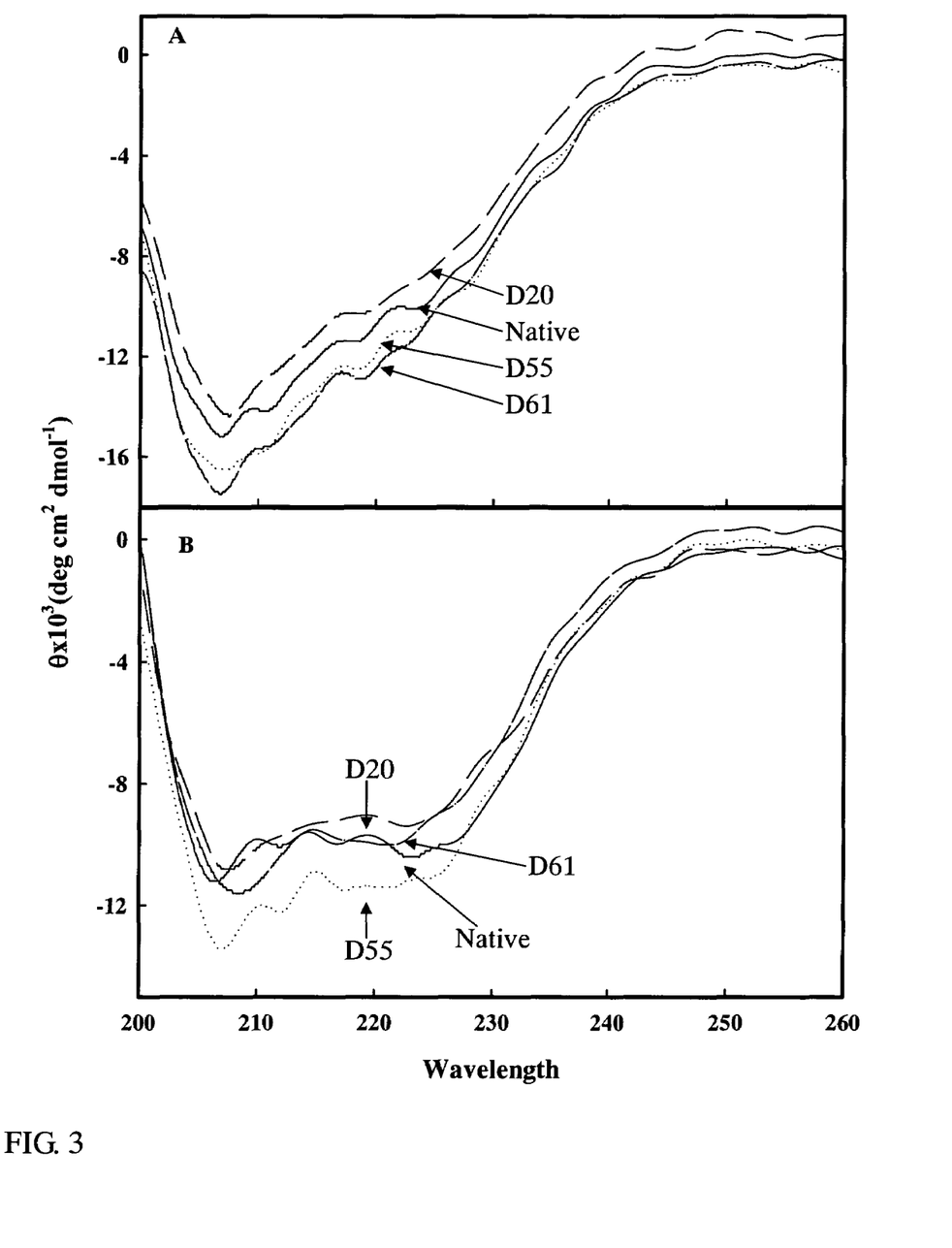
FIG. 3 shows a far UV circular dichroism analytical spectrum of the deamidated α-lactoalbumin in Example 3.

A similar sample was subjected to a far UV CD analysis, and the results are shown in FIG. 3. The analysis was conducted in a 20 mM Tris-HCl buffer (pH 7.0) containing 2 mM ethylenediamine tetraacetic acid (FIG. 3A) or 2 mM $CaCl_2$ (FIG. 3B). As evident from the figure, in any of the solution, each deamidated α-lactoalbumin exhibited a spectrum which was almost similar to that of the control non-deamidated α-lactoalbumin (native). Such findings suggest that the deamidated α-lactoalbumin underwent no change in the secondary structure.

As described above, it was revealed that a protein can be denatured by means of the deamidation by a protein deamidating enzyme. This denaturation state is a gently denatured state whose secondary structure is preserved while the tertiary structure was deteriorated, which is preferable for the functions of the protein.

EXAMPLE 4

Trypsin Digestion of α-lactoalbumin Treated by Protein Deamidating Enzyme

Figure 4:
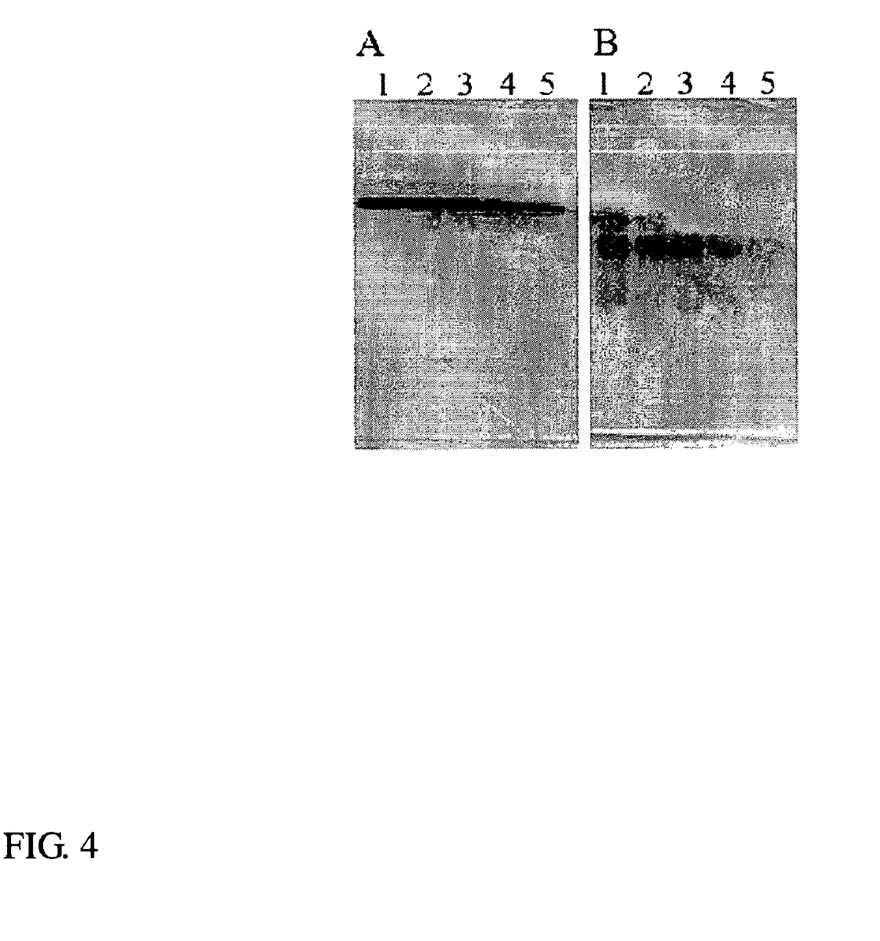
FIG. 4 shows the time course of the SDS polyacrylamide gel electrophoresis pattern of the trypsin-treated deamidated α-lactoalbumin in Example 4.

The deamidated α-lactoalbumin obtained in Example 2 (46.5% deamidation degree) was desalted by an ultrafiltration membrane, dissolved at 10 mg/ml in a 20 mM Tris-HCl buffer (pH 7.0) containing 2 mM $CaCl_2$, supplemented with a 1/100 amount of trypsin based on the weight of the substrate protein, and reacted at 37° C. As a control, a non-deamidated α-lactoalbumin was subjected to a similar treatment. After sampling at 0.5, 1, 2, 4 and 24 hours, the reaction was terminated by heating in a buffer for an SDS electrophoresis, and then an SDS-polyacrylamide gel electrophoresis was conducted. The results are shown in FIG. 4. As evident from this figure, the control non-deamidated α-lactoalbumin, when treated with trypsin, exhibited no change in the α-lactoalbumin band over a period of 4 hours during which the intact state was kept, showing almost no peptides decomposed into their lower molecular weight fragments, although the band became somewhat thinner at 24 hours (FIG. 4A). On the other hand, the deamidated α-lactoalbumin began to undergo the formation of fragmented peptides at the time as early as 0.5 hours after the trypsin treatment, which was accompanied with the reduction in the intact α-lactoalbumin band. At 1 hour after the reaction, a substantial amount of the intact α-lactoalbumin was lost, and a complete loss was observed at 2 hours. The fragmented peptides disappeared mostly at 24 hours, indicating the advancement of the degradation (FIG. 4B).

As described above, it was revealed that by denaturing a protein by means of the deamidation using a protein deamidating enzyme the degradation of an intended protein by the protease can be promoted.

INDUSTRIAL APPLICABILITY

As discussed above, by using denatured protein as a protein to be deamidated in the deamidation reaction of the protein using an enzyme which exerts a deamidating effect by acting directly on an amide group of the protein without cleaving a peptide bond or crosslinking the protein, the deamidation rate and the degree of deamidation can be markedly improved. In addition, by conducting a deamidation reaction using an enzyme which exerts a deamidating effect by acting directly on an amide group of the protein without cleaving a peptide bond or crosslinking the protein, the denaturation into a state exhibiting a high sensitivity to a protease can be accomplished. Since this denaturation method is an enzymatic protein denaturation method which is not known, it can avoid any side reactions which can not be avoided in a conventional physical or chemical protein denaturation method. Also since a protein obtained by an inventive denaturation method is highly sensitive to a protease, it can be used as a starting material to produce a protein degradation product at a high efficiency. Furthermore, an inventive method is advantageous also in terms of its ability of providing a protein whose emulsifying characteristics, foam characteristics and gelling characteristics are improved, since it can denature a protein under a gentle condition.

What is claimed is:

1. A method for deamidating a milk protein comprising bringing a denatured milk protein into contact with an enzyme which exerts a deamidating effect by acting directly on an amide group of a protein without cleaving a peptide bond or crosslinking the protein.

2. A method according to claim 1 wherein said enzyme is an enzyme having said effect on a protein having a molecular weight of 5,000 or more.

3. A method according to claim 1 wherein said enzyme is an enzyme having said effect on a protein having a molecular weight of 10,000 or more.

4. A method according to claim 1 wherein said enzyme is derived from a microorganism.

5. A method according to claim 4 wherein said microorganism belongs to a genus of *Chryseobacterium, Flavobacterium, Empedobacter, Sphingobacterium, Aureobacterium* or *Myroides*.

6. A method according to claim 4 wherein said microorganism is *Chryseobacterium* sp. No. 9670 (FERM BP-7351) belonging to the genus of *Chryseobacterium*.

7. A method according to claim 1 wherein said denatured milk protein is a denatured milk protein obtained by a denaturation treatment with one or more selected from the group consisting of heat, pressure, acid, alkali, denaturing agent, oxidant, reducing agent and chelating agent.

8. A method for producing a deamidated milk protein comprising:
   a step for denaturing a milk protein; and,
   a step for deamidating a denatured milk protein obtained in the previous step by bringing said denatured milk protein into contact with an enzyme which exerts a deamidating effect by acting directly on an amide group of a protein without cleaving a peptide bond or crosslinking the protein.

9. A method according to claim 8 wherein said enzyme is an enzyme having said effect on a protein having a molecular weight of 5,000 or more.

10. A method according to claim 8 wherein said enzyme is an enzyme having said effect on a protein having a molecular weight of 10,000 or more.

11. A method according to claim 8 wherein said enzyme is derived from a microorganism.

12. A method according to claim 11 wherein said microorganism belongs to a genus of *Chryseobacterium, Flavobacterium, Empedobacter, Sphingobacterium, Aureobacterium* or *Myroides*.

13. A method according to claim 11 wherein said microorganism is *Chryseobacterium* sp. No. 9670 (FERM BP-7351) belonging to the genus of *Chryseobacterium*.

14. A method according to claim 11 wherein said step for the denaturation consists of a treatment with one or more selected from the group consisting of heat, pressure, acid, alkali, denaturing agent, oxidant, reducing agent and chelating agent.

* * * * *